United States Patent [19]

Satzinger et al.

[11] Patent Number: 4,578,380

[45] Date of Patent: Mar. 25, 1986

[54] 5H-[1]BENZOPYRANO[2,3-D]PYRIMIDINE DERIVATIVES USEFUL FOR CONTROLLING LESIONS OF THE GASTRIC AND DUODENAL MUCOUS MEMBRANES

[75] Inventors: Gerhard Satzinger, Denzlingen; Hubert Barth, Emmendingen; Johannes Hartenstein, Stegen-Wittental; Manfred Herrmann; Edgar Fritschi, both of St. Peter; Ilse-Dore Schütt, Glottertal, all of Fed. Rep. of Germany

[73] Assignee: Warner-Lambert Company, Morris Plains, N.J.

[21] Appl. No.: 653,175

[22] Filed: Sep. 24, 1984

[30] Foreign Application Priority Data

Sep. 30, 1983 [DE] Fed. Rep. of Germany ....... 3335472

[51] Int. Cl.⁴ ............... A61K 31/505; C07D 491/052; C07D 491/153
[52] U.S. Cl. .................................. 514/232; 514/257; 514/267; 544/115; 544/247; 544/250
[58] Field of Search ............... 544/250, 115, 246, 247; 514/232, 257, 267

[56] References Cited

U.S. PATENT DOCUMENTS

| | | | |
|---|---|---|---|
| 3,272,811 | 9/1966 | Ohnacker et al. | 544/278 X |
| 3,468,888 | 9/1969 | Chow | 544/250 |
| 3,578,666 | 5/1971 | Manning | 544/278 X |
| 3,772,230 | 11/1973 | Hardtmann | 544/282 |
| 4,272,535 | 9/1981 | Blythin | 544/115 X |
| 4,297,355 | 10/1981 | Blythin | 544/115 X |

OTHER PUBLICATIONS

O'Callaghan, Chemical Abstracts, vol. 93, 220682j (1980).
O'Callaghan et al., Chemical Abstracts, vol. 100, 103286k (1984).

*Primary Examiner*—Donald G. Daus
*Assistant Examiner*—Diana G. Rivers
*Attorney, Agent, or Firm*—Ronald A. Daignault

[57] ABSTRACT

The invention relates to 5H-[1]benzopyrano-[2,3-d]pyrimidine derivatives of the general formula I

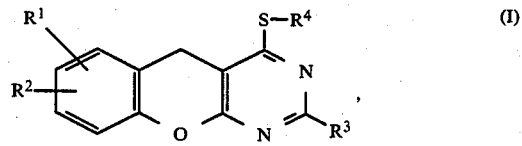

which may be prepared by means of a new chemical process and have a protective effect similar to that of cimetidine, but do not exhibit the undesired side effects of antisecretory agents. The invention is based on a new mucoprotective mode of action which prevents lesions of the mucous membrane epithelium to arise.

6 Claims, No Drawings

5H-[1]BENZOPYRANO[2,3-d]PYRIMIDINE DERIVATIVES USEFUL FOR CONTROLLING LESIONS OF THE GASTRIC AND DUODENAL MUCOUS MEMBRANES

SUMMARY OF THE INVENTION

The present invention relates to 5H-[1]benzopyrano[2,3-d]pyrimidine derivatives of the general formula I

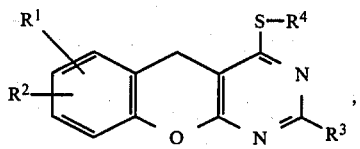

wherein $R^1$ and $R^2$, which may be the same or different, represent a hydrogen or halogen atom, a hydroxyl group or a straight-chain or branched alkoxy group with up to four carbon atoms, or together form an alkylenoxy- or alkylendioxygroup with one to three carbon atoms or represent a condensed aromatic ring, $R^3$ represents an optionally substituted phenyl radical, $R^4$ an alkyl group containing one to eight carbon atoms or the radical

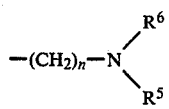

wherein $R^5$ and $R^6$, which may be the same or different, represent a hydrogen atom, a straight-chain or branched alkyl group with up to six carbon atoms or together with the nitrogen atom to which they are attached form a saturated five- or six-membered ring optionally containing further heteroatoms and n represents the integers 2 to 6, and their pharmacologically acceptable salts with organic or inorganic acids.

DETAILED DESCRIPTION

As the aromatic ring $R^1 R^2$ mainly the phenyl ring is possible, preferably the unsubstituted phenyl ring in 6,7-position.

As halogen atoms fluorine, chlorine, bromine, and iodine atoms come into consideration. Preference is accorded to the bromine atom.

As alkylenoxygroup there is preferred the ethylenoxy group forming an oxolene ring. As alkylenedioxygroup a methylenedioxy radical is preferred which forms a 1,3-dioxolene ring.

As the substituents of the phenyl radical $R^3$ come into consideration up to three substituents from the group of the halogen atoms, dialkylamino groups with up to four carbon atoms, or alkyl or alkoxy groups with up to four carbon atoms, and up to two alkylenedioxy groups with up to two carbon atoms.

The radicals $R^5$ and $R^6$ together with the nitrogen atom to which they are bound may form mainly pyrrolidino, piperidino, morpholino, or piperazino groups.

Preference is given to compounds of the general forumula I, in which $R^1$ and $R^2$ are the same or different, and represent a hydrogen or bromine atom, a hydroxyl, methoxy, or ethoxy group, or together an unsubstituted benzene ring condensed in 6,7 position, $R^3$ represents an unsubstituted or substituted phenyl radical, wherein the substituents may be a halogen atom, a dimethylamino, a methyl, a methylenedioxy group or up to three methoxy groups, $R^4$ is an alkyl group with up to four carbon atoms or the radical

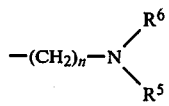

wherein $R^5$ and $R^6$ which may be the same or different represent a hydrogen atom, a methyl- or ethyl group or together with the nitrogen atom to which they are bound form a pyrrolidino-, piperidino-, morpholino-, or piperazino group and n represents the integers 2 or 3, as well as their pharmacologically acceptable acid salts.

Special preference is given to compounds of the general formula I, in which the radicals $R^1$ and $R^2$ are the same or different, and represent a hydrogen or bromine atom, or a methoxy group, $R^3$ a phenyl, 4-chlorophenyl, 4-dimethylaminophenyl, 4-methoxyhenyl, 4-hydroxyphenyl, 4-methylphenyl, or 3,4-methylendioxy- phenyl-radical, $R^4$ a n-hexylgroup, $R^5$ and $R^6$ both a methyl group and n the integers 2 and 3, as well as their pharmacologically acceptable acid addition salts.

Another subject matter of the invention is a chemically new process for the preparation of compounds of the general formula I, characterized by either (a) tautomerizing a compound of the general formula II,

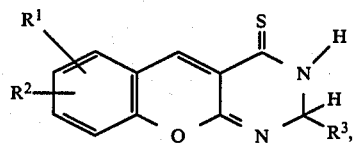

wherein the radicals $R^1$, $R^2$, and $R^3$ have the above meanings, in an organic solvent with a base, or (b) reacting a compound of the general formula III,

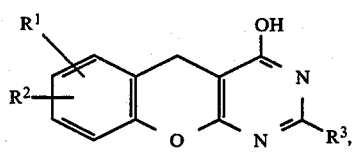

in which $R^1$, $R^2$, and $R^3$ have the above meanings, (1) with phosphorus pentasulfide in pyridine, and subsequently the compound, obtained by processes (a) or (b), of the general formula IV

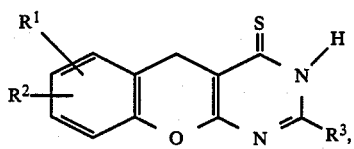

in which the radicals $R^1$, $R^2$, and $R^3$ have the above meanings, if desired being reacted with an alkylating agent of the general formula V $$X-R^4 \qquad (V),$$

in which the radical $R^4$ has the above meaning, and X represents a reactive ester group or (2) with inorganic acid halogenides, preferably with phosphorusoxychloride/phosphorus pentachloride to form compounds of the general formula VI

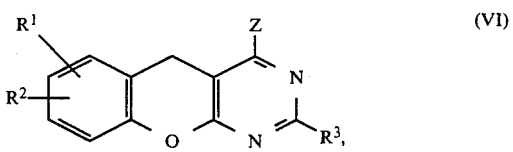

(VI)

wherein the radicals $R^1$, $R^2$, and $R^3$ have the above mentioned meaning and Z is a chloro- or bromo atom, whereafter the compounds of the general formula VI are reacted with a thioalcohol of the general formula IIIb $$HS—R^4 \quad (IIIb),$$

wherein $R^4$ has the above mentioned meaning with or without isolation, and the bases of the general formula I thus obtained subsequently being, if desired, transferred into pharmacologically compatible salts by means of the respective organic or inorganic acids in a generally known manner.

In the reaction of compounds of the general formula II with bases (reaction (a)) preferably polar solvents are used. Particularly suitable for this purpose are lower alcohols, such as e.g., methanol, ethanol, or n-butanol.

At increased temperature, preferably at the reflux temperature of the solvent, the reaction time usually is between about 5 and 30 minutes.

As preferred bases, potassium carbonate, potassium hydroxide, sodium methanolate, and sodium ethanolate are used. The reaction process may well be seen in the clearly visible clarification of the reaction mixture which first is mostly deep yellow to orange.

The starting compounds of the general formula II are also new compounds and are obtained by reacting compounds of the general formula VI,

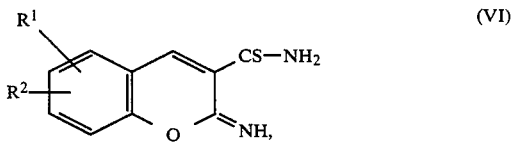

(VI)

in which $R^1$ and $R^2$ have the above meanings, and which are known from the DE-OS No. 2801353, with an aromatic aldehyde of the general formula VII, $$R^3—CHO \quad (VII),$$

in which $R^3$ has the above meaning, in the presence of a catalytic amount of a base, preferably at reflux temperature. Best suited bases proved to be piperidine and triethylamine. The water formed during the reaction is best removed azeotropically by the addition of a solvent immiscible with water, such as e.g., methylene chloride, chloroform, benzene, or toluene as an extracting medium.

As a rule the reaction lasts between six and 20 hours. The compounds of the general formula II, usually colored yellow to orange, usually are precipitated in the course of the reaction as sparingly soluble precipitates and may be isolated by suction, washing and drying, or they are obtained from the residue after removal of the solvent.

The starting thiocarbamoylchromene derivatives of the general formula VI are obtained according to DE-OS No. 2801353 by means of generally known procedures by reacting o-hydroxybenzaldehyde derivatives with 2-cyan-thioacetamide.

The starting products of the general formula III are described in J. Chem. Soc. p 1335, (1980).

The compounds of the general formula IV are preferably not isolated but in a direct way further reacted with compounds of the general formula V in a sort of a one-pot-process. By reactive ester groups are understood esters or semiesters of strong mineral acids such as e.g., hydrohalogenic acids or sulphuric acid. Preferred are the bromides and chlorides.

The compounds V are used in the form of their hydrobromides or hydrochlorides. In this case 2 mole equivalents of the base are used for the alkylation reaction.

The reaction of compounds of general formula VI is carried out in the presence of a base as e.g., sodium ethanolate or sodium methanolate in a polar solvent.

Following filtration from the precipitated alkali halide the compounds of the general formula I crystallize directly from the filtrate or are obtained after reduction of the reaction mixture and distribution of the residue between an organic solvent immiscible with water, such as e.g., methylene chloride or chloroform, and water, after concentration of the organic phase and crystallization from a suitable solvent.

The salts are obtained in the usual manner by neutralization of the bases with suitable inorganic or organic acids. As acids may be used, e.g., hydrochloric acid, sulphuric acid, phosphoric acid, hydrobromic acid, acetic acid, tartaric acid, lactic acid, citric acid, malic acid, salicylic acid, ascorbic acid, malonic acid, or succinic acid.

The compounds of the general formula I are valuable agents for the control of lesions of the gastric and duodenal mucous membranes.

The currently employed therapy of peptic ulcers consists either in inhibiting the acid secretion of the parietal cells of the stomach or in neutralizing the gastric acid before it comes into contact with the ulcerous areas. Therapy in this field of indication mainly employs pharmaceuticals of the group of anti-cholinergics or antacids. The former exhibit generally known side effects, the antacids have to be taken often and in large amounts.

A major turn in therapy came with the introduction of the histamine-$H_2$-receptor blocker cimetidine: it allowed a new form of antisecretory treatment. But cimetidine exhibits undesired CNS and other side effects; a particularly untoward effect are the changes of the gastric mucous membrane found under long-term treatment; this effect is responsible for relapse ulcers following discontinuation of cimetidine [Int. J. Clinical Pharmcol., Therapy and Toxicol. 18/3 (1980), pp 140–43].

The present invention is based on the idea that backing the *physiological* mechanisms of gastrointestinal mucous protection, i.e., *preventing* lesions of the mucosa epithelium, should be superior to any other therapy of ulcer disease, which after all is unphysiological. Inhibition, or even blocking, of peptic secretion as the objective of ulcer therapy means considerable disadvantages for the patient. There are scores of reports of duodenal mycosis, erosive, mycotic gastritis, and systemic candidiasis as the consequence of reduced resistance of gastric cells on the one hand, and an increase in the pH due to anti-secretion on the other hand. The present compounds according to the invention distinguish themselves by an excellent ulcer protective effect together with complete absence of ant.isecretory effects. Their cytoprotective effects against chemical noxae and stress factors make them seem suitable for the therapy of a series of indications. Such indications would be the gastric ulcer, gastritis, the duodenal ulcer and ulcerative colitis. They are also suited to back antirheumatic, steroidal, or cytostatic therapy.

The compounds of this invention may be used in all the common forms of application; preference being accorded to the oral forms. The application forms contain the usual excipients, fillings and lubricants and disintegrating additions. Such additions are, e.g., tartrate and citrate buffer, ethanol, complex formers (such as ethylene diamine tetra acetic acid and its nontoxic salts) as well as polymers of high molecular weight (such as liquid polyethylene oxide) to regulate the viscosity. Solid carrier substances are, e.g., starch, lactose, mannitol, methyl cellulose, talc, microdispersed silicic acid, fatty acids of high molecular weight (such as stearinic acid) gelatin, agar-agar, calcium phosphate, magnesium stearate, animal and vegetable fats, solid polymers of high molecular weight (such as polyethylene glycol); forms suited for oral administration may also contain in addition flavors and/or sweeteners, if desired.

Single doses preferably are in the range between 10 and 500 mg of the corresponding active ingredient.

Another subject matter of the invention therefore are pharmaceuticals marked by the fact that besides the usual filling and excipient materials they contain at least one compound of the general formula I, as well as the use of compounds according to the general formula I in the control of lesions of the gastric and duodenal mucous membranes.

The following examples serve to further explain the invention.

EXAMPLE 1

4-(3-dimethylaminopropylthio)-2-phenyl-5H-[1]benzopyrano[2,3-d]pyrimidine (1)

A mixture of 11.7 g 2,3-dihydro-2-phenyl-4-thioxo-[1]benzopyrano[2,3-d]pyrimidine, 11.5 g potassium carbonate and 300 ml ethanol is heated under reflux for 30 minutes. Subsequently, within 30 minutes, there is added drop by drop a solution of 6.3 g dimethylaminopropylchloride hydrochloride in 100 ml ethanol and the mixture is heated under reflux for another two hours. The hot reaction mixture is filtered, concentrated, and the residue crystallized from isopropanol. The yield is 8.7 g colorless crystals, mp 94° C.

The 2,3-dihydro-2-phenyl-4-thioxo-[1]benzopyrano[2,3-d]pyrimidine (28) used as the starting product is prepared in the following manner:

Ten (10.0) grams 2-imino-3-thiocarbamoyl-(2H)-chromene, 5.2 g benzaldehyde and five drops piperidine are boiled in 1 l benzene under a separator for six hours. When cool the precipitated yellow product of the reaction is sucked off, washed with a small volume of benzene and dried under a vaccum. Yield 11.0 g yellow crystals, mp 220° C., decomp.

In analogous manner the following compounds are obtained; 4-(2-diethylaminoethylthio)-2-phenyl-5H-[1]benzopyrano[2,3-d]pyrimidine (2) yield 71%, mp 109° C. and 4-(2-morpholinoethylthio)-2-phenyl-5H-[1]benzopyrano[2,3-d]pyrimidine (3) yield 77%, mp 155° C.

EXAMPLE 2

2-i4-chlorphenyl)-4-(2-piperidinoethylthio)-5H-[1]benzopyrano[2,3-d]pyrimidine (4)

One and six tenths (1.6) gram sodium are dissolved in 500 ml absolute ethanol. Then 11.4 g 2-(4-chlorophenyl)-2,3-dihydro-4-thioxo-benzopyrano[2,3-d]pyrimidine are added and the mixture is heated to boiling for 30 minutes. A solution of 6.4 g N-(2-chloroethyl)piperidine hydrochloride in 100 ml absolute ethanol is added drop by drop and again heated under reflux for one hour. The precipitate is cooled and sucked off, thoroughly washed with water and the residue subsequently crystallized from dimethylformamide.

Yield 12.1 g yellowish crystals, mp 179° C.

In analogous manner the following compounds are obtained:

2-(4-chlorophenyl)-4-(3-dimethylaminopropylthio)-5H-[1]benzopyrano[2,3-d]pyrimidine (5) yield 57%, mp 118° C.;

2-(4-chlorophenyl)-4-(2-diethylaminoethylthio)-5H-[1]benzopyrano[2,3-d]pyrimidine (6) yield 59%, mp 116° C.;

2-(4-dimethylaminophenyl)-4-(2-morpholinoethylthio)-5H-[1]benzopyrano[2,3-d]pyrimidine (7) yield 93%, mp 181° C.;

2-(4-dimethylaminophenyl)-4-(3-dimethylaminopropylthio)-5H-[1]benzopyrano[2,3-d]pyrimidine (8) yield 60%, mp 131° C.;

2-(4-dimethylaminophenyl)-4-(2-piperidinoethylthio)-5H-[1]benzopyrano[2,3-d]pyrimidine (9) yield 87%, mp 162° C.;

4-(3-dimethylaminopropylthio)-2-(3,4-methylenedioxyphenyl-5H-[1]benzopyrano[2,3-d]pyrimidine (12) yield 66%, mp 125° C.;

4-(2-dimethylaminoethylthio)-2-(3,4-methylenedioxyphenyl)-5H-[1]benzopyrano[2,3-d]pyrimidine (13) yield 70%, mp 167° C.;

4-(2-piperidinoethylthio)-2-(3,4,5-trimethoxyphenyl)-5H-[1]benzopyrano[2,3-d]pyrimidine (14) yield 84%, mp 168° C.;

4-(2-diethylaminoethylthio)-2-(4-methylphenyl)-5H-[1]benzopyrano[2,3-d]pyrimidine (15) yield 59%, mp 118° C.;

4-(3-dimethylaminopropylthio)-2-(4-methylphenyl)-5H1]benzopyrano[2,3-d]pyrimidine (16) yield 65%, mp 109° C.;

4-(2-morpholinoethylthio)-2-(4-methylphenyl)-5H-[1]benzopyrano[2,3-d]pyrimidine (17) yield 87%, mp 178° C.;

4-(3-dimethylaminopropylthio)-2-(4-methoxyphenyl-5H-[1]benzopyrano[2,3-d]pyrimidine (18) yield 70%, mp 100° C.;

4-(2-dimethylaminoethylthio)-7-methoxy-2-phenyl-5H-[1]benzopyrano[2,3-d]pyrimidine (19) yield 61%, mp 140° C.;

7-brom-4-(2-morpholinoethylthio)-2-phenyl-5H-[1]benzopyranol[2,3-d]pyrimidine (20) yield 73%, mp 190° C.;

9-ethoxy-2-phenyl-4-(2-pyrrolidinoethylthio)-5H-[1]benzopyrano[2,3-d]pyrimidine (21) yield 52%, mp 150° C.;

6,8-dimethoxy-2-phenyl-4-(2-piperidihoethylthio)-5H-[1]benzopyrano[2,3-d]pyrimidine (22) yield 55%, mp 165° C.;

4-(2-aminoethylthio)-2-phenyl-5H-[1]benzopyrano[2,3-d]pyrimidine (23) yield 70%, mp 152° C.;

4-(2-aminoethylthio)-7-methoxy-2-(4-methoxyphenyl)-5H-[1]benzopyrano[2,3-d]pyrimidine (24) yield 78%, mp 153° C.;

4-(2-aminoethylthio)-7-brom-2-(4-methoxyphenyl)-5H-[1]benxopyrano[2,3-d]pyrimidine (25) yield 60%, mp 196° C.;

2-(4-methylphenyl)-4-(3-morpholinopropylthio)-5H-[1]benzopyrano[2,3-d]pyrimidine (26) yield 73%, mp 139° C.;

4-(3-aminopropylthio)-2-(4-methylphenyl)-5H-[1]benzopyrano[2,3-d]pyrimidine (27) yield 32%, mp 131° C.;

11-(2-diethylaminoethylthio)-9-phenyl-12H-naphto-(1',2':5,6)pyrano[2,3-d]pyrimidine (27b) yield 70%, mp 174° C.;

4-(3-methylaminopropylthio)-2-(4-methylphenyl)-5H-[1]benzopyrano[2,3-d]pyrimidine (27a) yield 46%, mp 125°–127° C.;

4-2-diethylaminoethylthio)-2-(4-hydroxyphenyl)-5H-[1]benzopyrano[2,3-d]pyrimidine (10) yield 59%, mp 178° C.;

2-(4-hydroxyphenyl)-4-(2-morpholinoethylthio)-5H-[1]benzopyrano[2,3-d]pyrimidine (11) yield 47%, mp 225° C.;

4-hexylthio-2-(3,4-methylendioxyphenyl)-5H-[1]benzopyrano[2,3-d]pyrimidine (35) yield 68%, mp 111° C.;

4-(3-dimethylaminopropylthio)-2-(3,4,5-trimethoxyphenyl)-5H-[1]benzopyrano[2,3-d]pyrimidine (36) yield 70%, mp 162° C.;

4-(3-dimethylaminopropylthio)-7,8-methylendioxy-2-(3,4-methylendioxyphenyl)-5H-[1]benzopyrano[2,3-d]pyrimidine (37) yield 49%, mp 164° C.;

4-(6-dimethylaminohexylthio)-2-(3,4-methylendioxyphenyl)-5H-[1]benzopyrano[2,3-d]pyrimidine (38) yield 56%, mp 96° C., and 6-(3-dimethylaminopropylthio)-2,3-dihydro-8-(4-methylphenyl)-5H-furo[2',3':7,8][1]benzopyrano[2,3-d]pyrimidine (39) yield 69%, mp 171° C.

When preparing the compounds (10) and (11) there are used 3 mole equivalents sodium for the tautomerization reaction and the batch is worked up as follows:

The reaction mixture is concentrated in a rotary evaporator. The residue is then poured into 300 ml water and the pH adjusted to seven with diluted hydrochloric acid. The resulting precipitate is sucked off and crystallized from ethanol.

The 2-aryl-2,3-dihydro-4-thioxo-benzopyrano-(2,3-d)pyrimidines of the general formula II used to prepare said compounds are obtained according to example 1 by condensation of 2-imino-3-thiocarbamoyl-(2H)-chromenes of the general formula VI with suitable aldehydes of the general formula VII:

2-(4-chlorophenyl)-2,3-dihydro-4-thioxo-[1]benzopyrano[2,3-d]pyrimidine yield 61%, yellow crystals, mp 246° C., decomp.;

2-(4-dimethylaminophenyl)-2,3-dihydro-4-thioxo-[1]benzopyrano[

2,3-d]pyrimidine yield 63%, orange colored crystals, mp 218° C., decomp.;

2,3-dihydro-2-(4-hydroxyphenyl)-4-thioxo[1]benzopyrano[2,3-d]pyrimidine yield 80%, yellow crystals, mp 248° C., decomp.;

2,3-dihydro-2-(4-methylphenyl)-4-thioxo[1]benzopyrano[2,3-d]pyrimidine yield 52%, yellow crystals, mp 205° C., decomp.; 2,3-dihydro-2-(4-methoxyphenyl)-4-thioxo[1]benzopyrano[2,3-d]pyrimidine yield 52%, yellow crystals, mp 202° C., decomp.;

2,3-dihydro-2-(3,4-methylenedioxyphenyl)-4-thioxy-[1]benzopyrano[2,3-d]pyrimidine yield 56%, yellow crystals, mp 226° C., decomp.;

2,3-dihydro-2-(3,4,5-trimethoxyphenyl)-4-thioxo-[1]benzopyrano[2,3-d]pyrimidine yield 85%, yellow crystals, mp 290° C., decomp.;

2,3-dihydro-7-methoxy-2-phenyl-4-thioxo-[1]benzopyrano[2,3-d]pyrimidine yield 87%, yellow crystals, mp 223° C., decomp.;

9,10-dihydro-9-phenyl-11-thioxo-naphto(1',2':5,6)-pyrano[2,3-d]pyrimidine yield 85%, mp 320° C., decomp.;

7-bromo-2,3-dihydro-2-phenyl-4-thioxo-[1]benzopyrano[2,3-d]pyrimidine yield 80%, mp 330° C., decomp.;

9-ethoxy-2,3-dihyiro-2-phenyl-4-thioxo-[1]benzopyrano[2,3-d]pyrimidine yield 77%, mp 215° C., decomp.;

2,3-dihydro-6,8-dimethoxy-2-phenyl-4-thioxo-[1]benzopyrano[2,3-d]pyrimidine yield 68%, mp 298° C., decomp.;

2,3-dihydro-7-methoxy-2-(4-methoxyphenyl)-4-thioxo[1]benopyrano[2,3-d]pyrimidine yield 72%, mp 250° C., decomp.;

7-bromo-2,3-dihydro-2-(4-methoxyphenyl)-4-thioxo-[1]benzopyrano[2,3-d]pyrimidine yield 75%, mp 235° C., decomp.;

2,3-dihydro-7,8-methylenedioxy-2-(3,4-methylenedioxy- phenyl)-4-thioxo-[1]benzopyrano[2,3-d]pyrimidine yield 93%, mp 270° C., decomp.; and 2,3,7,8-tetrahydro-8-(4-methylphenyl)-6-thioxo-furo-(2',3':7,8][1]benzopyrano[2,3-d]pyrimidine yield 80%, mp >210° C. decomp.

EXAMPLE 3

2-phenyl-4-thioxo-3H,5H-[1]benzopyrano[2,3-d]pyrimidine (29)

One and one tenth (1.1) gram sodium are dissolved in 300 ml absolute ethanol. Fourteen and six tenths (14.6) gram 2,3-dihydro-2-phenyl-4-thioxo-[1]benzopyrano[2,3-d]pyrimidine are then added and the solution is heated to boiling for one hour. The reaction mixture is concentrated under a rotary evaporator, poured into 300 ml water and cautiously acidified with diluted hydrochloric acid. The precipitate is sucked off and crystallized from dimethylformamide/ethanol.

Yield 80%, yellow crystals, mp 245° C., (decomp.).

In an analogous manner there is obtained:

2-(4-dimethylaminophenyl)-4-thioxo-3H,5H-[1]benzopyrano[2,3-d]pyrimidine (30) yield 76%, yellow crystals, mp 245° C, decomp.;

2-(4-methoxyphenyl)-4-thioxo-3H,5H-[1]benzopyrano[2,3-d]pyrimidine (31) yield 74%, yellow crystals, mp 265° C., decomp.;

2-(4-chlorphenyl)-4-thioxo-3H,5H-[1]benzopyrano[2,3-d]pyrimidine (32) yield 70%, yellow crystals, mp 340° C., decomp.;

4-thioxo-2-(3,4,5-trimethoxyphenyl)-3H,5H-[1]benzopyrano[2,3-d]pyrimidine (33) yield 79%, ochre-colored crystals, mp 290° C., decomp.; and 2-(4-hydroxyphenyl)-4-thioxo-3H,5H-[1]benzopyrano[2,3-d]pyrimidine (34) yield 65%, yellowish crystals, mp 274° C., decomp.

EXAMPLE 4

4-(3-dimethylaminopropylthio)-2-phenyl-5H-[1]benzopyrano[2,3-d]pyrimidine

Eight and one tenth (8.1) gram 4-hydroxy-2-phenyl[1]benzopyrano[2,3-d]pyrimidine, 9.0 g phosphoruspentachloride and 36 ml phosphorusoxychloride are heated for two hours under reflux. Excess phosphorusoxychloride is then distilled off under a vacuum and the residue is partitioned to chloroform and water, a pH 6 value being adjusted by the addition of 10% sodium hydroxide. The organic phase is separated and the chloroform removed by distillation in a rotary evaporator. The residue obtained is separated by chromatography using cyclohexane/chloroform 1:1 as an eluting agent. There are obtained 4.0 g 4-chloro-2-phenyl[1]benzopyrano[2,3-d]pyrimidine, mp 168°–170° C. as colorless crystals. Thereafter 0.05 g sodium are dissolved in 10 ml anhydrous ethanol and 0.25 g 3-dimethylamino-1-propane-thiol added to the solution. The mixture obtained is added dropwise to a solution of 0.6 g 4-chloro-2-phenyl[1]benzopyrano[2,3-d]pyrimidine at reflux temperature. The reaction mixture is then kept under reflux for another two hours. After cooling the reaction mixture is filtered and the filtrate is evaporated to dryness and the residue partitioned to chloroform and water. The organic phase is separated off, the chloroform is evaporated and the residue recrystallized from ethanol. There are obtained 0.4 g colorless crystals, mp 93° C.

In an analogous manner there is obtained:

4-(4-dimethylaminobutylthio)-2-(3,4-methylenedioxyphenyl)-5H-[1]benzopyrano[2,3-d]pyrimidine, yield 64%, mp 97°–98° C.

The following comparative tests demonstrate the novel mode of action of the compounds according to the general formula I in comparison to cimetidine.

Pharmacological Methods

1. Indomethacin-Induced Ulcer

Test animals were male rats (Sprague Dawley SIV 50) weighing between 150–200 g. The animals were kept fasting 24 hours before starting the test, drinking water being available ad libitum. The animals were alloted to three groups, each group comprising ten rats. Ulcerations were created by administering 40 mg/kg i.g. doses of indomethacin to all animals. The groups received simultaneously either the vehicle (control group) the suspension of the active principle (test group) or a reference substance (cimetidine 100/200 mg/kg). Five hours following administration the animals were killed with $CO_2$ gas, the stomachs removed and opened along the greater curvature.

After measuring the pH value the stomach was tested for ulcerations under a stereo magnifying glass. The method described by Chaumontet, et al. Arzneimittel-forschung/Drug Research 28 (II) pp 2119–2121 (1978) was used to rate the ulcerations and calculate the ulcer index (UI). The effect of the substances was rendered as the percentage inhibition of the ulcers caused by indomethacin in comparison to the untreated reference group.

2. Cold-Stress Ulcer

Test animals were male rats (Sprague Dawley SIV 50) weighing between 110 and 150 g. The animals were kept fasting 24 hours before starting the test, drinking water being available ad libitum.

The rats were alloted to three groups each comprising ten animals, one group receiving the vehicle substance (0.8% methocel), the second group the test substance suspended in 0.8% methocel, and the third group a reference standard (cimetidine 50 mg/kg) i.g. Immediately after administration of the substances the animals were anesthetized with penthrane and, lying on their backs, fixed with adhesive tapes to wooden boards.

Thus rendered immobile the animals were put into a permanently lit room, ambient temperature +15° C., relative humidity 50–60%, for 14 hours.

After this time of exposure the rats were killed with $CO_2$, the stomachs removed and opened along the greater curvature.

After measuring the pH value the gastric mucosa was tested for ulcerations under a stereo magnifying glass.

The ulcerations were rated and the ulcer index (UI) calculated as described for test 1, the effect of the substances being expressed as the percentage inhibition of the ulcer formation in comparison to the untreated control group.

3. Test for the Inhibition of the Gastric Acid Secretion According to Ghosh and Schild (Brit. J. Pharmacol. 13 pp 54–61 (1958)

The test animals were male rats (Sprague Dawley SIV 50) weighing between 300–450 g. The animals were kept fasting 24 hours before starting the test, water being available ad libitum.

The animals were anesthetized with 1.25 g/kg urethane IP.

Trachea, vena jugularis, arteria carotis, and oesophagus were exposed, and a fistula placed at the pylorus. Via an oesophagus tube the stomach was perfused with 1/4000 N NaOH at a flow rate of 3 ml/min. By means of the NaOH perfusion the pH of the gastric juice was adjusted to about pH 7 and continuously measured with a measuring electrode.

Via the vena jugularis the acid-stimulating substance (carbachol 0.25 µg/kg/min or pentagastrin 1 µg/kg/min) was infused. When a maximum secretion (pH 3.5) was achieved the test substance suspended in 0.8% methocel could be applied via a duodenal catheter.

One hour following application of the test substance the secretion inhibiting reference substance cimetidine was given in a dose of 30 mg/kg i.d. The test was terminated when the starting pH of 7 was reached again.

Test for Acute Toxicity

Method:

The acute toxicity was determined in male mice (NMRI) weighing between 20 and 25 g. All test animals were kept fasting for 20 hours before starting the test, water being available ad libitum. Each dosage group comprised four animals. The dose sequence was logarithmic. The test substances were administered suspended in 0.8% methocel in an application volume of 20 mg/kg body weight. The animals were observed for altogether seven days.

Dosages corresponding to $LD_{50}$-values over 1600 mg/kg were not considered in order to spare animals.

The following table shows the results of the above tests.

TABLE

| Substance | Dose mg/kg i.g. | Ulcer Models: Protective Action in % | | Antisecretion (Gosh + Schild Model) | $LD_{50}$ (Mouse) mg/kg i.g. (7-Day Values) |
| --- | --- | --- | --- | --- | --- |
| | | "Indomethacin" | "Stress" | | |
| Compound (1) | 125 | 88 | 70 | No effect | >1.600 |
| | 250 | 95 | 86 | No effect | |
| Compound (16) | 125 | 83 | 72 | No effect | >1.600 |
| | 250 | 99.5 | | No effect | |
| Compound (26) | 250 | 50 | | No effect | >1.600 |
| Compound (27a) | 250 | 94 | | No effect | >1.600 |
| Cimetidine | 5 i.v. | | | pH 7.9 after 35 min | |
| | 100 | 80 | 53 | | 2.600 |
| | 200 | 89 | 54 | | |
| | 3 × 100 | | 39 | | | i.v. = intraveneous application
i.g. = intragastral application

The results of the reference tests show that the compounds of the general formula I give in both ulcer models a highly protective effect, markedly superior to that of cimetidine. In no case, do the substances according to the invention exhibit an antisecretory effect. In all compounds tested the toxicity is over 1,600, i.e., in the same order as that of cimetidine.

Thus, we can say that the compounds according to the invention are a highly potent type of ulcer-protective substance without entailing any serious side effects.

We claim:

1. A 5H-[1]benzopyrano-[2,3-d]pyrimidine derivative of the formula I,

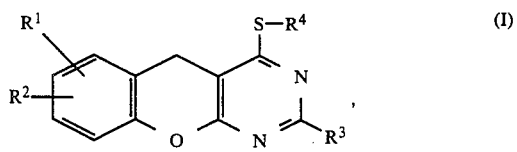

wherein $R^1$ and $R^2$, which may be the same or different, represent a hydrogen or halogen atom, a hydroxyl group or a straight-chain or branched alkoxy group with up to four carbon atoms, or together form an alkylenoxy- or alkylenedioxy group with one to three carbons atoms or, together an unsubstituted benzene ring condensed in 6,7-position, $R^3$ represents an optionally substituted phenyl radical, $R^4$ an alkyl group containing one to eight atoms or the radical,

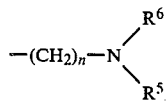

wherein $R^5$ and $R^6$, which may be the same or different, represent a hydrogen atom, a straight-chain or branched alkyl group with up to six carbon atoms or together with the nitrogen atom to which they are attached form a pyrrolidino-, piperidino-, morpholino-, or piperazino group and n represents the integers two to six, or a pharmacologically acceptable salt with an organic or inorganic acid.

2. A compound according to claim 1, in which $R^1$ and $R^2$ are the same or different, and represent a hydrogen or bromine atom, a hydroxyl, methoxy, or ethoxy group, or together an unsubstituted benzene ring condensed in 6,7 position, $R^3$ represents an unsubstituted or substituted phenyl radical, wherein the substitutents may be a halogen atom, a dimethylamino, a methyl, a methylenedioxy group or up to three methoxy groups, $R^4$ is an alkyl group with up to four carbon atoms or the radical

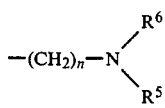

wherein $R^5$ and $R^6$ which may be the same or different represent a hydrogen atom, a methyl- or ethyl group or together with the nitrogen atom to which they are bound form a pyrrolidino-, piperidino-, morpholino- or piperazino group and n represents the integers 2 or 3.

3. A compound according to claim 1, in which $R^1$ and $R^2$ are the same or different and represent a hydrogen or bromine atom, or a methoxy group; $R^3$ is a phenyl, 4-chlorophenyl, 4-dimethylaminophenyl, 4-methoxyphenyl, 4-hydroxyphenyl, 4-methylphenyl or 3,4-methylenedioxyphenyl radical; $R^4$ is n-hexyl; $R^5$ and $R^6$ are both methyl, and n is 2 or 3.

4. A compound according to claim 1 and being 4-(3-dimethylaminopropylthio)-2-phenyl-5H-[1]benzopyrano[2,3-d]pyrimidine.

5. A pharmaceutical composition for controlling lesions of the gastric and duodenal mucous membranes comprising an effective amount of a compound according to claim 1, together with pharmaceutically acceptable fillers and excipients.

6. A method of controlling lesions of the gastric and duodenal mucous membranes in a subject suffering from ulcers comprising administering to said subject an effective amount of a pharmaceutical composition according to claim 5.

* * * * *